(12) United States Patent
Hodes et al.

(10) Patent No.: US 7,412,938 B2
(45) Date of Patent: Aug. 19, 2008

(54) STRUCTURED SURFACES WITH CONTROLLED FLOW RESISTANCE

(75) Inventors: Marc Scott Hodes, New Providence, NJ (US); Paul Robert Kolodner, Hoboken, NJ (US); Thomas Nikita Krupenkin, Waren, NJ (US); Joseph Ashley Taylor, Springfield, NJ (US); Ryan Maurice Enright, Longford (IE)

(73) Assignees: Lucent Technologies Inc., Murray Hill, NJ (US); University of Limerick, Limerick (IE)

( * ) Notice: Subject to any disclaimer, the term of this patent is extended or adjusted under 35 U.S.C. 154(b) by 302 days.

(21) Appl. No.: 11/227,735

(22) Filed: Sep. 15, 2005

(65) Prior Publication Data

US 2007/0059489 A1    Mar. 15, 2007

(51) Int. Cl.
*B63B 1/34* (2006.01)
(52) U.S. Cl. .................................. 114/67 R; 359/665
(58) Field of Classification Search ............... 114/67 R; 359/665; 366/127; 239/44; 264/291, 320, 264/339
See application file for complete search history.

(56) References Cited

U.S. PATENT DOCUMENTS

| | | | |
|---|---|---|---|
| 3,454,686 A | 7/1969 | Jones | |
| 3,670,130 A | 6/1972 | Greenwood | |
| 4,030,813 A | 6/1977 | Kohashi et al. | |
| 4,118,270 A | 10/1978 | Pan et al. | |
| 4,137,060 A | 1/1979 | Timmermann | |
| 4,338,352 A | 7/1982 | Bear et al. | |
| 4,406,732 A | 9/1983 | Kayoun | |
| 4,569,575 A | 2/1986 | Le Pesant et al. | |
| 4,653,847 A | 3/1987 | Berg et al. | |
| 4,671,609 A | 6/1987 | Khoe et al. | |
| 4,708,426 A | 11/1987 | Khoe et al. | |
| 4,783,155 A | 11/1988 | Imataki et al. | |
| 4,784,479 A | 11/1988 | Ikemori | |
| 4,867,521 A | 9/1989 | Mallinson | |
| 4,948,214 A | 8/1990 | Hamblen | |
| 5,248,734 A | 9/1993 | Ober et al. | |
| 5,348,687 A | 9/1994 | Beck et al. | |
| 5,412,746 A | 5/1995 | Rossberg et al. | |
| 5,428,711 A | 6/1995 | Akiyama et al. | |
| 5,486,337 A | 1/1996 | Ohkawa | |

(Continued)

FOREIGN PATENT DOCUMENTS

DE    19623270 A    1/1998

(Continued)

OTHER PUBLICATIONS

U.S. Appl. No. 10/040,017, filed Jan. 4, 2002, Megens et al.

(Continued)

*Primary Examiner*—Lars A Olson

(57) ABSTRACT

An apparatus comprising a substrate having a surface configured to accommodate a fluid thereover. A plurality of fluid-support-structures are on the surface. Each of the fluid-support-structures has at least one dimension of less than one millimeter. A well in the substrate has an opening on the surface. A medium is locatable between the plurality of fluid-support-structures and in the well. The medium located between the fluid-support-structures is in communication with the medium in the well.

9 Claims, 12 Drawing Sheets

U.S. PATENT DOCUMENTS

| | | | |
|---|---|---|---|
| 5,518,863 | A | 5/1996 | Pawluczyk |
| 5,659,330 | A | 8/1997 | Sheridon |
| 5,665,527 | A | 9/1997 | Allen et al. |
| 5,922,299 | A | 7/1999 | Bruinsma et al. |
| 5,948,470 | A | 9/1999 | Harrison et al. |
| 6,014,259 | A | 1/2000 | Wohlstadter |
| 6,027,666 | A | 2/2000 | Ozin et al. |
| 6,185,961 | B1 | 2/2001 | Tonucci et al. |
| 6,329,070 | B1 | 2/2001 | Sass et al. |
| 6,319,427 | B1 | 11/2001 | Ozin et al. |
| 6,369,954 | B1 | 4/2002 | Berge et al. |
| 6,379,874 | B1 | 4/2002 | Ober et al. |
| 6,387,453 | B1 | 5/2002 | Brinker et al. |
| 6,409,907 | B1 | 6/2002 | Braun et al. |
| 6,465,387 | B1 | 10/2002 | Pinnavaia et al. |
| 6,471,761 | B2 | 10/2002 | Fan et al. |
| 6,473,543 | B2 | 10/2002 | Bartels |
| 6,538,823 | B2 | 3/2003 | Kroupenkine et al. |
| 6,545,815 | B2 | 4/2003 | Kroupenkine et al. |
| 6,545,816 | B1 | 4/2003 | Kroupenkine et al. |
| 6,891,682 | B2 | 5/2005 | Aizenberg et al. |
| 2002/0125192 | A1 | 9/2002 | Lopez et al. |
| 2003/0020915 | A1 | 1/2003 | Schueller et al. |
| 2003/0148401 | A1 | 8/2003 | Agrawal et al. |
| 2004/0069195 | A1* | 4/2004 | Goldstein ................. 114/67 R |
| 2004/0191127 | A1 | 9/2004 | Komblit et al. |
| 2005/0039661 | A1 | 2/2005 | Komblit et al. |
| 2005/0069458 | A1 | 3/2005 | Hodes et al. |

FOREIGN PATENT DOCUMENTS

| | | |
|---|---|---|
| DE | 197 05 910 | 6/1998 |
| DE | 197 04 207 A1 | 8/1998 |
| EP | 0 290 125 | 11/1988 |
| EP | 1120164 | 8/2001 |
| FR | 2769375 | 4/1999 |
| FR | WO 99/18456 | 4/1999 |
| WO | WO 99/54730 | 10/1999 |
| WO | WO 01/31404 A1 | 5/2001 |
| WO | WO 01/42540 | 6/2001 |
| WO | WO 01/51990 | 7/2001 |
| WO | WO 03/056330 | 7/2003 |
| WO | WO 03/071335 | 8/2003 |
| WO | WO 03/083447 | 10/2003 |
| WO | WO 03/103835 | 12/2003 |

OTHER PUBLICATIONS

U.S. Appl. No. 10/094,093, filed Mar. 8, 2002, Eggleton et al.
U.S. Appl. No. 10/096,199, filed Mar. 12, 2002, Chandross et al.
U.S. Appl. No. 10/098,286, filed Mar. 15, 2002, Chen et al.
U.S. Appl. No. 10/135,973, filed Apr. 30, 2002, Z Bao et al.
U.S. Appl. No. 10/139,124, filed May 3, 2002, Kroupenkine et al.
U.S. Appl. No. 10/231,614, filed Aug. 30, 2002, Kroupenkine et al.
U.S. Appl. No. 10/321,027, filed Dec. 17, 2002, Reichmanis et al.
U.S. Appl. No. 10/383,150, filed Mar. 6, 2003, Chen et al.
U.S. Appl. No. 10/402,046, filed Mar. 28, 2003, Aizenberg et al.
U.S. Appl. No. 10/403,159, filed Mar. 31, 2003, Komblit et al.
U.S. Appl. No. 10/631,996, filed Jul. 31, 2003, Aizenberg et al.
U.S. Appl. No. 10/637,837, filed Aug. 8, 2003, Davis et al.
U.S. Appl. No. 10/649,285, filed Aug. 27, 2003, Kornblit et al.
U.S. Appl. No. 10/674,448, filed Sep. 30, 2003, Hodes et al.
U.S. Appl. No. 10/716,084, filed Nov. 18, 2003, Kroupenkine et al.
U.S. Appl. No. 10/798,064, filed Mar. 11, 2004, Amey et al.
U.S. Appl. No. 10/803,565, filed Mar. 18, 2004, Hodes et al.
U.S. Appl. No. 10/803,576, filed Mar. 18, 2004, Kroupenkine et al.
U.S. Appl. No. 10/803,641, filed Mar. 18, 2004, Hodes et al.
U.S. Appl. No. 10/806,543, filed Mar. 23, 2004, Amey et al.
U.S. Appl. No. 10/810,774, filed Mar. 26, 2004, Krouopenkine et al.
U.S. Appl. No. 10/816,569, filed Apr. 1, 2004, Gasparyan et al.

Washizu, Masao, "Electrostatic Actuation of Liquid Droplets for Microreactor Applications," IEEE Transactions on Industry Applications, vol. 34, No. 4, Jul./Aug. 1998, pp. 732-737.
Schilling, Andreas et al., Surface Profiles of Reflow Microlenses Under the Influence of Surface Tension and Gravity, Opt. Eng. (39(8) pp. 2171-2176, Society of Photo-Optical Instrumentation Engineers, Aug. 2000.
Danzerbrink, R. et al., "Deposition of Micropatterned Coating Using an Ink-Jet Technique," Thin Solid Films 351, pp. 115-118, Elsevier Science S.A. (1999).
Feng, Chuan Liang et al., "Reversible Wettability of Photoresponsive Flourine-Containing Azobenzene Polymer in Langmuir-Blodgett Films," Lengmuir vol. 17, No. 15, 2001, pp. 4593-4597, American Chemical Society published on Web Jun. 22, 2001.
Ichimura, Kunihiro et al., "Light-Driven Motion of Liquids on a Photoresponsive Surface." Science. vol. 288. Jun. 2, 2000. pp. 1624-1626.
Commander, L.G. et al., "Variable Focal Length Microlenses," Optics Communications 177. Apr. 15, 2000. pp. 157-170.
Aizenberg, J., et al., "Calcitic microlenses as part of the photoreceptor system in brittlestars." Nature. vol. 412, pp. 819-822. Aug. 23, 2001.
English language translation of abstract for German Patent Document: DE 19623270 from European Patent Office database, esp@cenet.com, (1998), 1 page.
Tuberfield, A.J., "Photonic Crystals Made By Holographic Lithography," MRS. Bulletin. Aug. 2001. pp. 632-636.
Campbell, M., et al., "Fabrication of Photonic Crystals For The Visible Spectrum by Holographic Lithography," Nature, vol. 404, Mar. 2, 2000, pp. 52-56.
Ho, K.M., et al., "Existence Of A Photonic Gap In Periodic Dielectric Structures," Physical Review Letters, vol. 65, No. 25, Dec. 17, 1990, pp. 3152-3155.
Ozbay, E., et al., "Measurement Of A Three-Dimensional Photonic Band Gap In A Crystal Structure Made Of Dielectric Rods," Physical Review B, vol. 50, No. 3, Jul. 15, 1994, pp. 1945-1948.
Tuberfield, A., "Photonic Crystals Made By Holographic Lithography," Abstract from Symposium K, Microphotonics-Materials, Phyisics, and Applications, Nov. 26-29, 2001, 1 page.
Shoji, S., et al., "Photofabrication Of Three-Dimensional Photonic Crystals By Multibeam Laser Interference Into A Photopolymarizable Resin," Applied Physics Letters, vol. 76, No. 19, May 8, 2000, pp. 2668-2670.
Sundararajan, N., et al., "Supercritical CO2 Processing for Submicron Imaging of Fluoropolymers," Chemistry of Materials, vol. 12, No. 1, Jan. 2000, pp. 41-48.
Kresge, C.T., et al: "Ordered mesoporous molecular sievas synthesized by a liquid-crystal template mechanism" Nature, vol. 359, Oct. 1992, pp. 710-712.
Tanev, Peter T., et al: "A Neutral Templating Route to Mesaporous Molecular Sieves." Science. vol. 267, Feb. 1995. pp. 855-867.
Huo, Q. et al: "Generalized synthesis of periodic surfactant/inorganic composite materials." Nature, vol. 368, Mar. 1994. pp. 317-321.
Sanchez, C., et al: "Design and Properties of Hybrid Organic-Inorganic Nanocomposites for Photonics." MRS Bulletin. May 2001. pp. 377-387.
Yang, P., et al: "Hierarchically Ordered Oxides," Science, vol. 282, Dec. 1998, pp. 2244-2246. Templin, M. et al: "Organically Modified Aluminosilicate Mesostructures from Block Copolymer Phases," Science vol. 278 Dec. 1997 pp. 1795-1798.
Raman, N.K., et al: "Template-Based Approaches to the Preparation of Amorphous, Nanoporous Silicas," Chemical Matter, vol. 8, Feb. 1996, pp. 1682-1701.
Yang, P., et al: "Block Copolymer Templating Synthesis of Mesoporous Metal Oxides with Large Ordering Lengths and Semicrystalline Framework," Chemical Matter, vol. 11, 1999, pp. 2813-2826.
Brinker, C.J., et al., "Evaporation-Induced Self-Assembly: Nanostructures Made Easy**'" Advanced Materials. vol. 11. 1999. pp. 579-585.
Lee, Y-J., Braun, P.V., "Tunable Inverse Opal Hydrogel pH Sensors," Adv. Mater. 2003. 15. No. 7-8. Apr. 17, 2003. pp. 563-566.

Arsenault, A.C., et al., "A Polychromic, Fast Response Metallopolymer Gel Photonic Crystal with Solvent and Redox Tunability: A Step Towards Photonic Ink (P-Ink)," Adv. Mater. 2003, 15, No. 6, Mar. 17, 2003, pp. 503-507.

Zhang, S., et al., "Materials and techniques for electrochemical biosensor design and construction," Biosensors & Bioelectronics 15, (2000), pp. 273-282.

Wu, H., et al., "Reduction Photolithography Using Microlens Arrays: Applications in Gray Scale Photolithography," Analytical Chemistry, vol. 74, No. 14, Jul. 15, 2002, pp. 3267-3273.

Leister Microsystems, leaflet by Leister Microsystems entitled, "Micro-optics—Imagine the Future of Light." Sep. 2000. 4 pages.

Stokes, D.L., et al., "Detection of E. coli using a microfluidics-based Antibody Biochip detection systems," Fresenius, J. Anal Chem (2001) 369, pp. 295-301.

Jahns, J., et al., "Microoptics for biomedical applications," American Biotechnology Laboratory. No. 18. Oct. 2000, pp. 52 and 54.

Campbell, D.J., et al., "Replication and Compression of Bulk and Surface with Pholydimethylsiloxane Elastomer," Journal of Chemical Education, vol. 75, No. 4, Apr. 1999, pp. 537-541.

Kruk, M., et al., "Mesoporous Silicate-Surfactant Composites with Hydrophobic Surfaces and Tailored Pore Sizes"; Journal of Physical Chemistry 106 B (2002) pp. 10096-10101.

Thrush, E., et al., "Integrated semiconductor fluorescent detection system for biochip and biomedical applications," IEEE-EMBS Special Topic Conference on Microtechnologies in Medicine & Biology, May 2002, pp. 374-379.

Avgeropoulos, et al., "Synthesis and Morphological Behavior of Silicon-Containing Triblock Copolymers for Nanostructure Applications," Chem. Mater. 1998, 10, pp. 2109-2115.

Chan, Vanessa A-H., et al., "Ordered Biocontinuous Nanoporous and Nanorelief Ceramic Films from Self-Assembling Polymer Precursors," Science, Nov. 26, 1999, vol. 286, pp. 1716-1719.

Shishido, A., et al., "Direct fabrication of two-dimensional titania arrays using interference photolithography," Applied Phyiscal Letters, vol. 79, No. 20, Nov. 12, 2001, pp. 3332-3334.

Young, "Organic-Inorganic Monomers," accessed at http://www.psrc.usm.edu/mauritz/nano2.html. Jul. 8, 2002.

Yang, et al., "Creating Periodic Three-Dimensional Structures by Multibeam Interference of Visible Laser," Chemistry of Materials, vol. 14, No. 7, Jul. 2002, pp. 2831-2833.

Vlasov et al., "On-Chip Netural Assembly of Silicon Photonic Bandgap Crystals." Nature. vol. 414. Nov. 15, 2001, pp. 289-293.

Baney, et al., "Silsesquioxanes," American Chemical Society, 1995, pp. 1409-1430.

The Wittman Company, "Carbon Dioxide," published online at http://www.witteman.com/co2.htm. Dec. 4, 2002, 2 pages.

"Sol-Gel Chemistry," published online at http://www.sol-gel.com/chemi.htm, Dec. 9, 2002. 2 pages.

Abbot, N.L., et al., "Potential-Dependent Wetting of Aqueous Solutions on Self-Assembled Monolayers Formed from 15-(Ferrocenylcarbonyl) pentadecanethiol on Gold," Langmuir 1994, American Chemical Society vol. 10, pp. 1493-1497.

Abbot, N.L., et al. "Potential-Dependent Wetting of Aqubous Solutions on Self-Assembled Monolayers Formed from 15-(Ferrocenylcarbonyl) Pentadecanethiol on Gold," Langmuir 1994, American Chemical Soceity vol. 10, pps. 1493-1497.

Kim, et al, "Nanostructured Surfaces for Dramatic Reduction of Flow Resistance in Dropllet-Based Microfluidics." IEEE. pp. 479-482 (2002).

E.W. Becker, et al., "Fabrication of microstructures with high aspect ratios and great structural heights by synchrotron radiation lithography, galvanoforming, and plastic moulding (LIGA process)", Microelectronic Engineering Elsevier Publishers RV, Amsterdam, NL, vol. 4, No. 1, (May 1, 1986) pp. 35-56.

Surface Energy Material (dynes/cm), ACCUDYNETE, "Solid Surface Energies," accessed at http://www.accudynetest.com/surface_energy_materials.html, Jul. 27, 2005 (3 pages).

eFunda: General Information on Element Silicon, accessed at http://www.efunda.com/materials/elements/element_info.cfm?Element_ID=Si, Aug. 10, 2005 (8 pages).

Bhardwaj, et al., "Advances in High Rate Silicon and Oxide Etching using ICP", STS Ltd., Imperial Park, Newport, UK NP10 89UJ (6 pags).

Templin, et al., "Organically Modified Aluminosilicate Mesostructrures from block Copolymer Phases", www.sciencemag.org, Science, vol. 278, Dec. 5, 1997, pp. 1795-1798.

Glod, et al., "An investigation of microscale explosive vaporization of water on an utrathin Pt wire", International Journal of Heat and Mass Transfer 45 (2002), pp. 367-379.

Four (4) European Search Reports each dated Sep. 15, 2004.

Aizenberg, et al., patent application for "A Low Adsorption Surface" filed Aug. 31, 2005.

* cited by examiner

US 7,412,938 B2

STRUCTURED SURFACES WITH CONTROLLED FLOW RESISTANCE

TECHNICAL FIELD OF THE INVENTION

The present invention is directed, in general, to controlling the flow resistance of a fluid on a surface.

BACKGROUND OF THE INVENTION

There is great interest in engineering surfaces to reduce the flow resistance of a liquid on the surface. Some structured surfaces having nanometer- or micron-sized raised features have promise in applications ranging from the transport of a liquid through a microfluidic channel, to reducing the drag of a vessel traveling through a liquid. However, a number of problems must be overcome before the full benefit of these surfaces can realized.

One problem is that the flow resistance of a liquid on a structured surface can vary dramatically with the pressure of the liquid. If the pressure of the liquid increases, then the liquid will penetrate to a greater extent into the structured surface, thereby increasing the flow resistance of the liquid on that surface. Alternatively, if the pressure of the liquid decreases, then the liquid will penetrate to a lesser extent into the structured surface, thereby decreasing the flow resistance. Flow resistance can also increase when the diffusion of air out of the liquid is sufficient to form air bubbles on the structured surface. For instance, the formation of air bubbles on the interior walls of a microfluidic channel can significantly impede the flow of liquid through the channel.

Embodiments of the present invention overcome these deficiencies by providing an apparatus having a structured surface with improved pressure stability, which thereby provides better control over flow resistance, as well as methods of using and manufacturing such an apparatus.

SUMMARY OF THE INVENTION

To address the above-discussed deficiencies, one embodiment of the present invention is an apparatus. The apparatus comprises a substrate having a surface configured to accommodate a fluid thereover. The surface comprises a plurality of fluid-support-structures thereon. Each of the fluid-support-structures has at least one dimension of less than one millimeter. A well in the substrate has an opening on the surface. A medium is locatable between the plurality of fluid-support-structures and in the well, and the medium located between the fluid-support-structures is in communication with the medium in the well.

Another embodiment is a method of use. The method comprises controlling a flow resistance of a fluid disposed on a surface of a substrate. The method includes forming a medium-fluid interface by contacting the fluid with a plurality of the above-described fluid-support-structures on the surface, the fluid-support-structures having a medium located there-between. The method further comprises communicating the medium between the fluid-support-structures and a well in the substrate, thereby stabilizing a location of the medium-fluid interface over the surface.

Yet another embodiment comprises a method of manufacture. The method comprises forming a well in a substrate, the well having an opening on a surface of the substrate. The method further includes forming a plurality of the above-described fluid-support-structures on the surface. The fluid-support-structures and the well are configured to allow a medium to communicate between the fluid-support-structures and the well.

BRIEF DESCRIPTION OF THE DRAWINGS

The invention is best understood from the following detailed description, when read with the accompanying figures. Various features may not be drawn to scale and may be arbitrarily increased or reduced for clarity of discussion. Reference is now made to the following descriptions taken in conjunction with the accompanying drawings, in which.

DETAILED DESCRIPTION

Embodiments of the present invention benefit from the detailed study of the hydrodynamics of various structured surfaces. It has been discovered that the poor pressure stability of certain structured surfaces is due to the inability to maintain a substantial pressure difference between the fluid over the surface and a medium in the structured surface. The term medium, as used herein, refers to any gas or liquid that is locatable in the structured surface. The term fluid refers to any gas or liquid that is locatable in or on the structured surface. In some cases, for example, the medium comprises air and the fluid comprises water. If the surface tension between the fluid and the medium becomes unable to keep the fluid-medium interface in place at the top of the structured surface, then the fluid can penetrate the structured surface. Consequently, fluid flow over the surface is impeded.

It was realized as part of the present invention that pressure stability is improved, and hence flow resistance better controlled, by incorporating one or more wells into certain structured surfaces. The well can accommodate the medium, and the medium located in the well can communicate with the medium located in the structured surface. The well is configured so that fluid preferentially enters the well instead of the structured surface when fluid pressure increases. At the same time, medium is expelled from the well into the structured surface, thereby maintaining the fluid-medium interface in one location. When the fluid pressure decreases, the fluid exits the well and medium is concurrently drawn from the structured surface into the well, again maintaining the fluid-medium interface in place. Additionally, it was realized that the well can receive medium that diffuses out of the fluid, thereby deterring the formation of medium on the structured surface.

Figure 1:
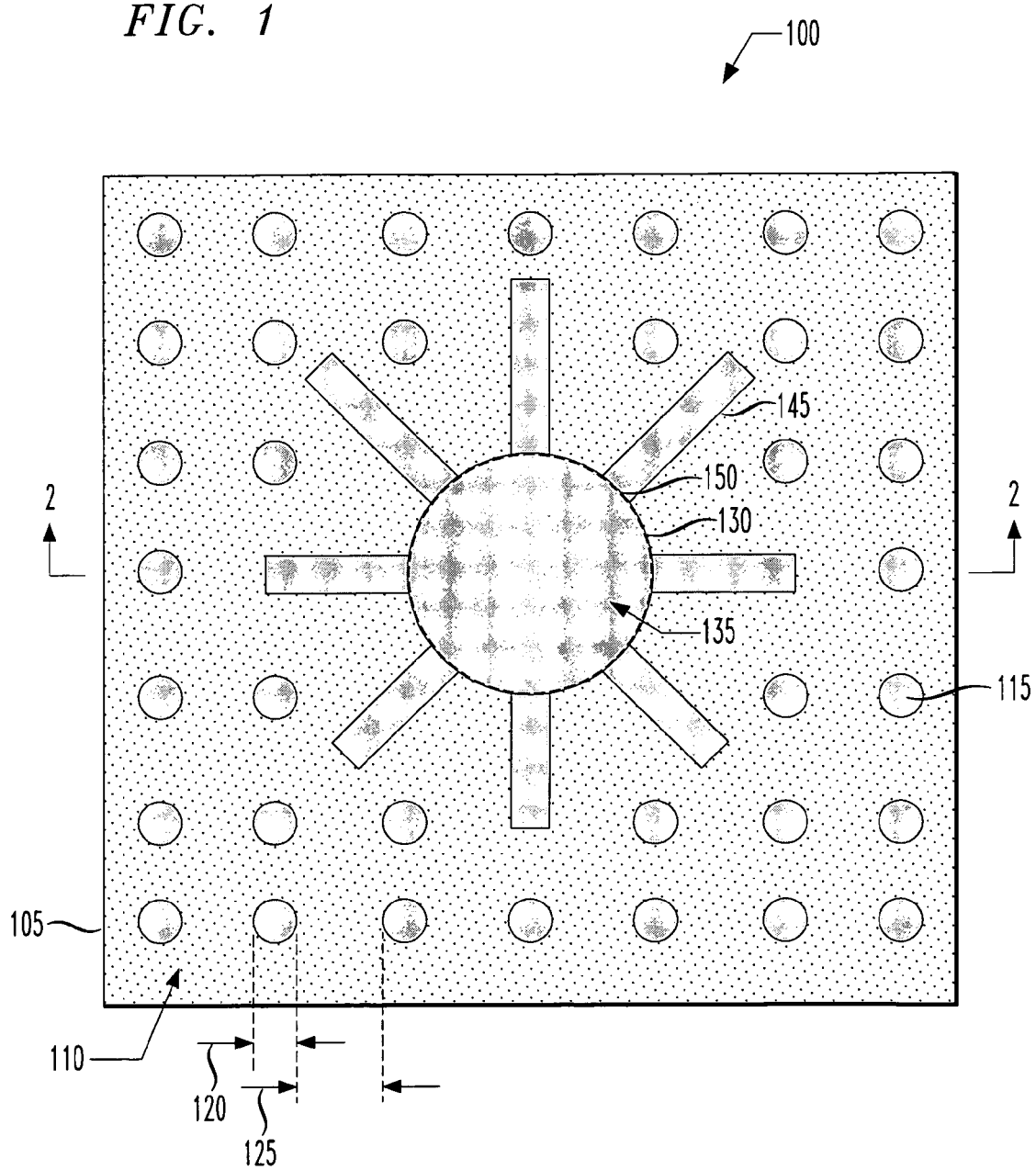
FIG. 1 presents a plan view of an exemplary apparatus.
Figure 2:
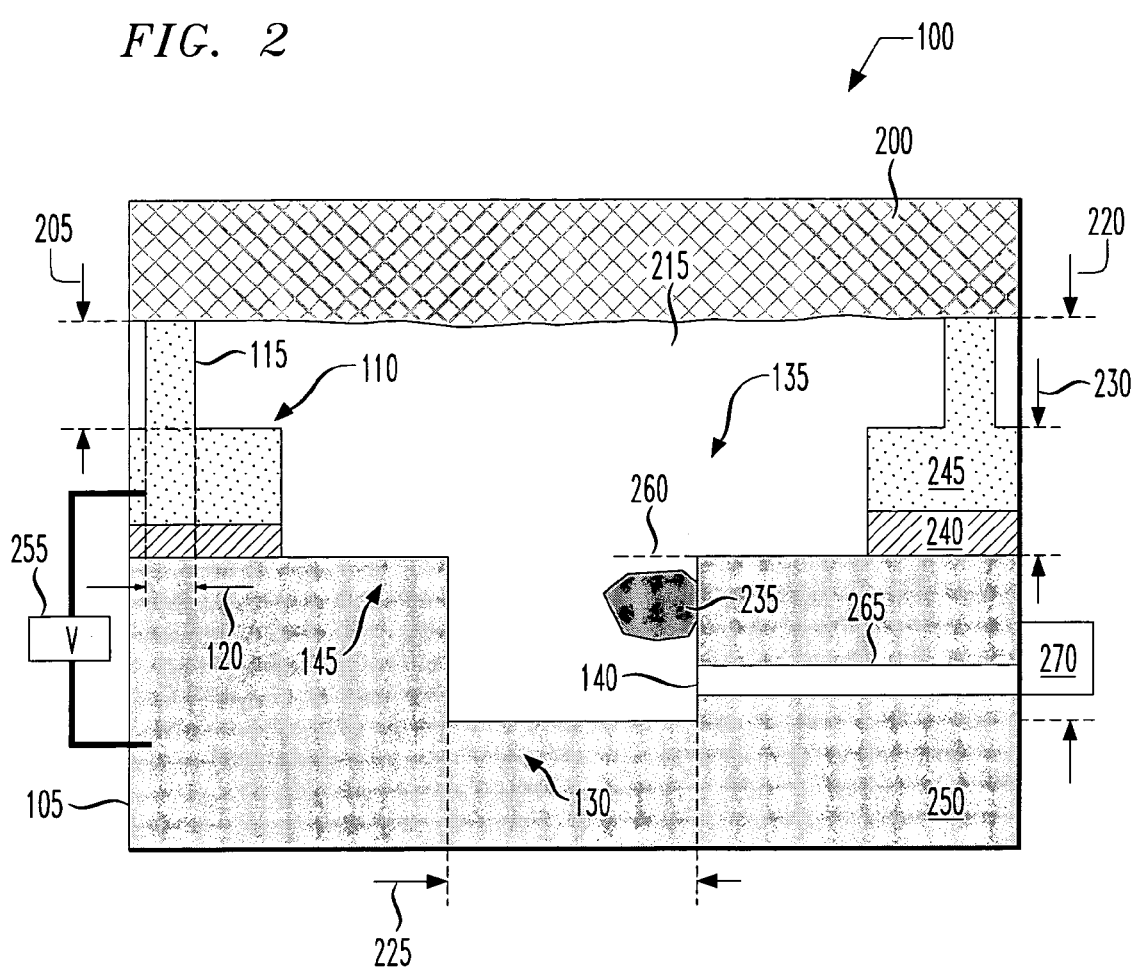
FIG. 2 shows a cross-section view of the apparatus along view lines 2-2 in FIG. 1.

One embodiment of the present invention is an apparatus. FIG. 1 presents a plan view of an exemplary apparatus 100 to illustrate certain features of the present invention. FIG. 2 shows a cross-section view of the apparatus 100 along view lines 2-2 in FIG. 1.

As illustrated in FIG. 1, the apparatus 100 comprises a substrate 105 having a surface 110. As illustrated in FIG. 2, the surface 110 is configured to accommodate a fluid 200 thereover. As further illustrated in FIGS. 1-2, the surface 110 comprises a plurality of fluid-support-structures 115 on the surface 110. For the particular embodiment of the apparatus 100 shown in FIGS. 1-2, the fluid-support-structures 115 are posts, and more specifically cylindrically-shaped posts. The term post as used herein, includes any structure having cylindrical, cubic, rectangular prism, conical, pyramidal or other geometric shapes.

In some preferred embodiments, conductive fluid-support-structures 115 are electrically coupled to a conductive substrate 105. As discussed in U.S. Patent Application 2004/0191127, in such embodiments, the fluid-support-structures 115 are coated with an electrical insulator. In other cases, the fluid-support-structures 115 are also coated with a low surface energy material. Examples of suitable electrical insulators and low surface energy materials are dielectric materials like silicon oxide, and fluoropolymers like polytetrafluoroethylene, respectively. In other cases, the fluid-support-structures 115 are coated with a material, such as Cytop® (Asahi Glass Company, Limited Corp. Tokyo, Japan), a fluoropolymer that is both an electrical insulator and a low surface energy material.

Each of the fluid-support-structures 115 can comprise microstructures, nanostructures, or both. The term microstructure as used herein refers to a predefined raised feature on a surface that has at least one dimension that is about 1 millimeter or less. The term nanostructure as used herein refers to a predefined raised feature on a surface that has at least one dimension that is about 1 micron or less.

For the embodiment of the apparatus 100 presented in FIG. 1, the one dimension that is about 1 millimeter or less, or about 1 micron or less, is a lateral thickness 120 the post. In cases where the fluid-support-structures 115 are cylindrically-shaped posts, the lateral thickness 120 corresponds to the diameter of the post. As illustrated in FIG. 2, in some cases each of the fluid-support-structures 115 can have a uniform height 205 ranging from about 1 to about 10 microns and a diameter 120 of about 1 micron or less.

In some cases it is advantageous to arrange the fluid-support-structures 115 into a two-dimensional array such as illustrated in FIG. 1. Additionally, the fluid-support-structures 115 can have a uniform separation 125 from each other. For example, the separation 125 between adjacent fluid-support-structures 115 can be a uniform distance ranging from about 1 to about 10 microns. However, in other cases, the separation 125 can be non-uniform.

The apparatus 100 further includes a well 130 in the substrate 105. The well 130 has an opening 135 on the same surface 110 that comprises the plurality of fluid-support-structures 115. In some instances, the well 130 has a cylindrical shape, such as depicted in FIGS. 1-2. However, the well 130 can have a variety of alternative shapes, such as a cube or rectangular prism. Of course, the well 130 can be coated with one or both of an electrical insulator and low surface energy material, similar to that described above for the fluid-support-structures 115.

As illustrated in FIG. 2, a medium 215 is locatable between the plurality of fluid-support-structures 115. For example, the medium 215 can comprise a layer of gas, such as air, located adjacent the substrate surface 110 and between the fluid-support-structures 115. Additionally, the medium 215 is locatable in the well 130. The medium 215 located between the fluid-support-structures 115 is in communication with the medium 215 in the well 130. For example, there is direct communication for the embodiment illustrated in FIGS. 1-2 when portions of the medium 215 move back and forth from the well 130 to between the fluid-support-structures 115.

As also depicted in FIG. 2, in some preferred embodiments, the well 130 is located below the surface 110 on which the fluid-support-structures 115 are formed. In such embodiments, the opening 135 of the well 130 is substantially flush with the surface 110, and a wall 140 of the well 130 is inside of the substrate 105. Locating the well 130 below the surface 110 facilitates communication of the medium 215 between the plurality fluid-support-structures 115 with the medium in the well 130. In other cases, however, the well 130 could have walls 140 that extend above the substrate surface 110, so long as the medium 215 in the well 130 can still communicate with the medium between the fluid-support-structures 115, for example through an opening in the well 130.

It is desirable for the well 130 to be configured to contain a sufficiently large volume of the medium 215 to accommodate a broad range of fluid pressures that may be exerted on the surface 110. In some cases, the well 130 is configured to contain a volume of the medium 215 that is equal to or greater than a volume of the medium 215 located between the fluid-support-structures 115. In other cases, the well 130 is configured to contain a volume of the medium 215 that is at least about 10 times greater than a volume of the medium 215 located between the fluid-support-structures 115.

In some preferred embodiments of the apparatus 100, the substrate 105 has more than one well 130. Having more than one well 130 facilitates containing a larger volume of the medium 215 than would be possible if one were to use a single well 130. For instance, in some cases there is at least one well 130 per about 1 to about 10 millimeter$^2$ area of the substrate surface 110.

With reference to FIG. 2, in some embodiments of the apparatus 100, the well 130 has a depth 220 in the range of about 10 to about 100 microns and a width 225 in the range of about 100 to about 1000 microns. To facilitate the penetration of the fluid 200 into the well 130 but not the fluid-support-structures 115, at least one lateral dimension of the well 130 is substantially larger than the separation 125 between adjacent ones of the fluid-support-structures 115. In some cases, at least one lateral dimension of the well 130 ranges from about 10 to about 100 times greater than the separation 125 between adjacent ones of the fluid-support-structures 115. In some cases, the one lateral dimension is the well's width 225. In instances where the well 130 has a cylindrical shape, such as depicted in FIG. 1, the one lateral dimension is the well's diameter 225.

It is also preferable for at least one lateral dimension of the well 130 to be less than a capillary length of the fluid 200. For the purposes of the present invention, a capillary length is defined as the distance between the walls 140 of the well 130 where the force of gravity becomes equal to the surface tension for the fluid 200 located on the well 130. Consider, for example, the situation where the fluid 200 is water, and the capillary length for water equals about 2.5 millimeters. In this case, for some embodiments, the well's width 225 is constrained to about 2.5 millimeters or less. Again, when the well 130 has a cylindrical shape, the well's diameter 225 is preferably less than the capillary length of about 2.5 millimeters.

It is advantageous for the medium 215 in the fluid-support-structures 115 to have direct access to the well 130. In some cases, any medium 215 located between the fluid-support-structures 115 is within about 1000 microns of the wall 140 of the well 130. In other cases, any of the medium 215 located between the fluid-support-structures 115 is within about 100 microns of the wall 140.

Turning to FIG. 1, in some cases, to facilitate communication between the medium 215 in the fluid-support-structures 115 and medium 215 in the well 130, the well 130 comprises one or more arms 145. In some cases, such as illustrated in FIG. 1, the arms 145 project out from the well's central perimeter 150. The medium 215 in the arms 145 is in communication with the medium 215 in the well 130 and with medium 215 between the fluid-support-structures 115. As illustrated in FIGS. 1 and 2, the arms 145 can have a rectangular prism shape. However, other geometric shapes can be used. Any of the above-discussed constraints concerning the communication of medium 215 from between the fluid-support-structures 115 and well 130, or the location and size of the well 130, are also applicable to the arms 145. It is advantageous for the area of each arm 145 to be substantially less than the area of the central well 130 so that a large portion of the surface 110 can be covered with the fluid-support-structures 115 and fluid 200 thereon. In some cases, the area of each arm 145 ranges from about one-half to about one-tenth of the area of the central well 130. In other cases a depth 230 of the arms is equal to or less than the depth 220 of the well 130.

In some cases, the substrate 105 is a planar substrate, and more preferably, a stack of planar substrates that are in contact with each other. For instance, the substrate 105 can comprise an inorganic semiconductor, such as silicon or silicon-on-insulator (SOI). In other instances, however, the substrate 105 can comprise other materials, such as plastics or metals.

In some cases, the medium 215 that is locatable between the fluid-support-structures 115 and in the well 130 can be depleted, for example, by diffusing into the fluid 200. In other cases, the amount of medium 215 locatable in the well 130 is less than desired. This can arise in situations, for example, where a high pressure of fluid 200 is being exerted against the surface 110. In such instances, it is advantageous for the apparatus 100 to include components that facilitate the production of additional medium.

For example, as further illustrated in FIG. 2, the apparatus 100 can be configured to electrolytically convert portions of the fluid 200 into additional medium 235. The substrate 105 can comprise an insulating layer 240 located between an upper conductive layer 245 and a lower conductive layer 250. For instance, the substrate 105 can comprise a SOI substrate where the insulating layer 240 comprises silicon oxide and the upper and lower conductive layers 245, 250 comprise silicon. Additionally, the apparatus 100 can include an electrical source 255 that is configured to apply a voltage (V) between the upper and lower conductive layers 245, 250. In some cases, the electrical source 255 is configured to apply the voltage when the fluid 200 penetrates into the well 130 below a plane 260 of the insulating layer 240. The voltage applied by the electrical source 255 thereby facilitates the electrolytic generation of additional medium 235 inside the well 130. In some cases, for instance, when the fluid 200 comprises water, the applied voltage facilitates the electrolytic generation of additional medium 235 comprising oxygen and hydrogen.

Of course, the additional medium 235 is not necessarily the same substance as the original medium 215. For instance, in some cases, the medium 215 comprises air, while the additional medium comprises oxygen and hydrogen gas. Also, the additional medium 235 can be added to the well 130 in ways other than electrolysis. For example, the well 130 can be coupled to one or more channel 265 embedded in the substrate 105. The channel 265 can be configured to supply or remove medium 215, or additional medium 235, as needed using an external pressure control device 270.

Figure 3:
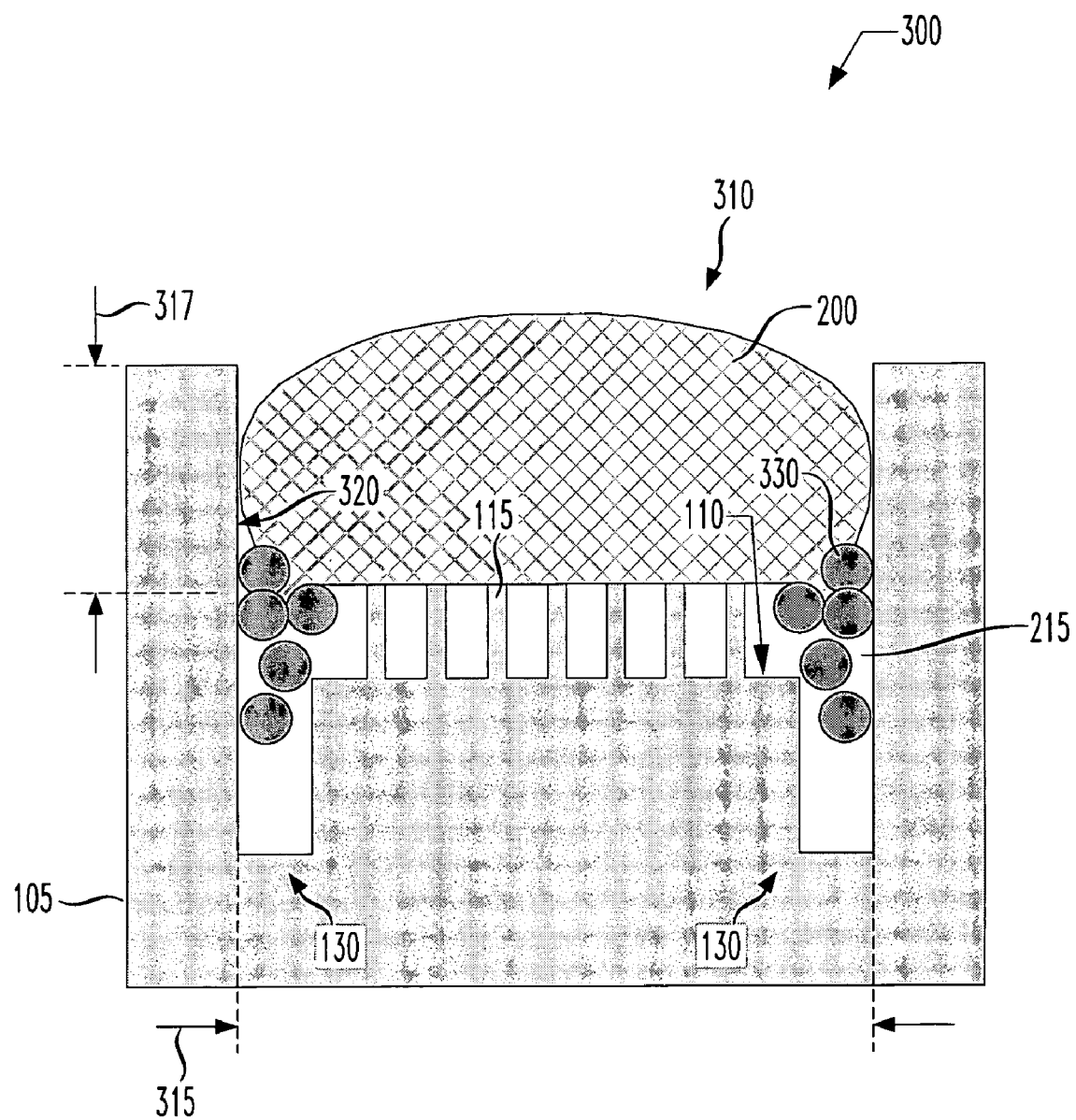
FIG. 3 shows a cross-sectional view of an apparatus of the present invention comprising a microfluidic device.

One of ordinary skill in the art would appreciate that various embodiments of the apparatus of the present invention could be used in a myriad of situations where it is desirable to control the flow resistance of a fluid. As one example, turning to FIG. 3, shown is cross-sectional view of an apparatus 300 of the present invention comprising a microfluidic device, that is, a channel 310 having at least one dimension that is about 1 millimeter or less. For instance, both the width 315 and height 317 of the channel 310 can be about 1 millimeter or less.

With continuing reference to FIG. 1-2, the substrate surface 110 comprising the fluid-support-structures 115 corresponds to an interior surface of a channel 310 that is configured to transport the fluid 200. The substrate 105 comprises at least a portion of the structure that defines the channel 310. In some preferred embodiments, the well 130 in the substrate 105 is configured to be located along sides 320 of the channel 310. Such a configuration can be desirable in situations where the formation of a gas 330, due to the diffusion of gas out of the fluid 200, could impede the flow of fluid 200. For instance, one or more gas bubble 330 forming in the channel 310 could obstruct the flow of fluid 200 through the channel 310. In such instances, the gas 330 preferably goes into the well 130, thereby allowing fluid 200 to flow through the channel 310 unimpeded by the gas 330.

Figure 4:
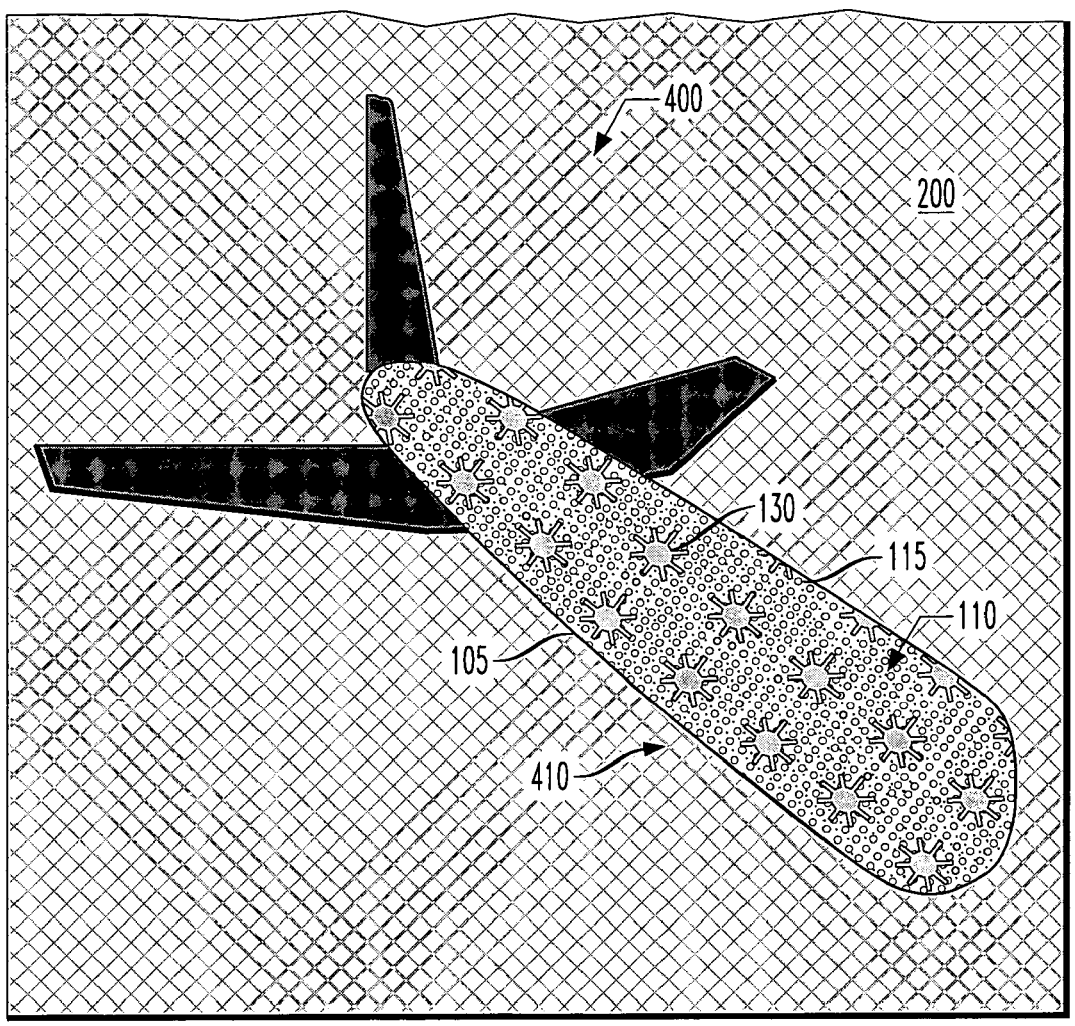
FIG. 4 shows a perspective view of an apparatus that comprises a vehicle.

As another example, turning to FIG. 4, shown is a perspective view of an apparatus 400 that comprises a vehicle, such as an on-water or underwater vehicle. With continuing reference to FIG. 1-2, the substrate 105 comprises at least a portion of a body of the apparatus 400, and the substrate surface 110 is an external surface of the body 410. The body 410 is configured to move through or on the fluid 200. In some cases, for example, the body 410 comprises a hull of the vehicle. Providing fluid-support-structures 115 on the substrate 105 and wells 130 in the substrate 105 facilitates the movement of the apparatus 400 through the fluid 200 because the flow resistance is reduced as compared to an apparatus not having the fluid-support-structures 115 and wells 130 thereon. Preferably, the flow resistance experienced by the apparatus 400 is maintained constant as it moves through the fluid 200 at different fluid 200 pressures or concentrations of gases dissolved in the fluid. Consider, for example, when the apparatus 400 is an underwater vehicle and the fluid 200 comprises a body of water, such as an ocean. The reduced flow resistance of the apparatus 400 is maintained while moving through the fluid 200 at different depths in the fluid 200, or at different concentrations of air dissolved in the fluid 200. As an indicator of the extent of reduced flow resistance, one could compare the lower amount of power used to propel the apparatus 400 through the fluid 200 at a given velocity to the amount of power used to propel an apparatus not having the fluid-support-structures 115 and wells 130.

Another aspect of the present invention is a method of use. FIGS. 5-8 present cross-sectional views of an exemplary apparatus 500 at various stages of controlling the flow resistance of a fluid disposed on a surface of a substrate. The views are analogous to the view presented in FIG. 2 but at lower magnification and with no arms projecting from the well. Any of the various embodiments discussed above and illustrated in FIGS. 1-5 could be used in the method. FIGS. 5-8 use the same reference numbers to depict analogous structures to that shown in FIGS. 1-4.

Figure 5:
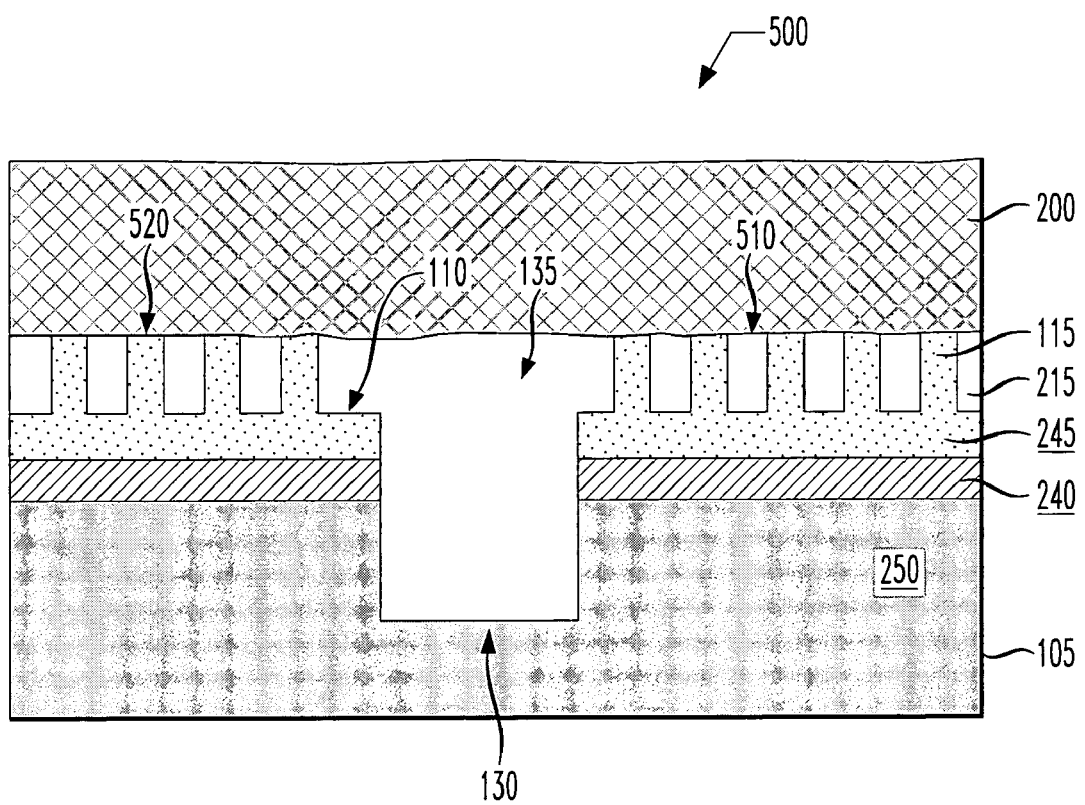
FIGS. 5-8 present cross-section views of an exemplary apparatus at various stages of a method of use according to the present invention.
Figure 6:
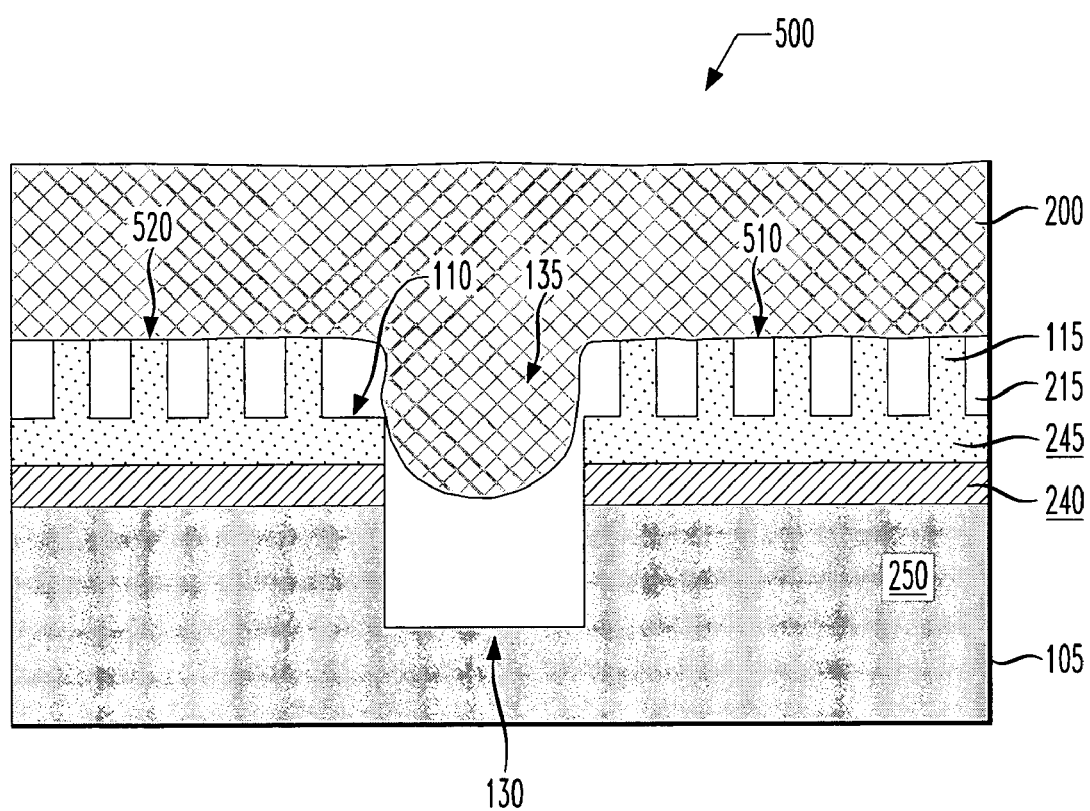

Turning to FIG. 5, illustrated is the apparatus 500 after contacting a fluid 200 with a plurality of fluid-support-structures 115 on a surface 110 of a substrate 105. Contact may occur, for example, by putting the apparatus 500 on or in the fluid 200, or, by putting the fluid 200 on or in the apparatus 500. As discussed above, each of the fluid-support-structures 115 has at least one dimension of less than one millimeter and a medium 215 locatable there-between. The fluid 200 and medium 215 form a medium-fluid interface 510. The apparatus 500 is configured to facilitate the communication of the medium 215 between the fluid-support-structures 115 and a well 130 in the substrate 105, thereby stabilizing a location of the medium-fluid interface 510 over the surface 110.

Preferably, the medium-fluid interface 510 is located on the tops 520 of the fluid-support-structures 115, with substantially no contact between the fluid 200 and the underlying substrate surface 110. Locating the fluid 200 on the tops 520 of the fluid-support-structures 115 is desirable because this minimizes the contact area between the fluid 200 and fluid-support-structures 115. This, in turn, minimizes the flow resistance of the fluid 200 over the substrate surface 110. In other instances, however, the medium-fluid interface 510 can be located below the tops 520 of the fluid-support-structures 115, but preferably does not contact the substrate surface 110.

While maintaining reference to FIGS. 1-5, FIG. 6 illustrates the apparatus 500 while communicating medium 215 by expelling the medium 215 from the well 130 to between the fluid-support-structures 115. The expulsion of medium 215 occurs when the fluid 200 penetrates the well 130. The penetration of fluid 200 into the well 130 can occur when the fluid pressure is increased. The fluid pressure may increase, for example, because the apparatus 500 is at an increased depth in the fluid 200, the temperature of the fluid 200 has increased, or the fluid 200 is being pumped through a channel. As discussed above, the well 130 is configured so that the fluid 200 preferentially enters the well 130 instead of the fluid-support-structures 115. As the fluid 200 enters the opening 135 of the well 130, medium 215 is expelled from the well 130 to between the fluid-support-structures 115. This, in turn, maintains the fluid-medium interface 510 at a constant height with respect to the substrate surface 110, preferably at or near the tops 520 of the fluid-support-structures 115, so that the flow resistance is maintained constant. For example, in some cases, the fluid 200 does not penetration by more than about 10 percent of a height 205 of the fluid-support-structures 115.

With continuing reference to FIGS. 1-6, FIG. 7 illustrates the apparatus 500 while communicating medium 215 by drawing the medium 215 from between the fluid-support-structures 115 to the well 130. Drawing medium from between the fluid-support-structures 115 occurs when the fluid 200 exits the well 130. The fluid 200 can exit the well 130 when the fluid pressure is decreased. A decreased fluid pressure may occur, for example, because the apparatus 500 is at a decreased depth in the fluid 200, the temperature of the fluid has decreased, or the fluid 200 is no longer being pumped through a channel. As the fluid 200 exits the opening 135 of the well 130, medium 215 is drawn from between the fluid-support-structures 115 to the well 130. Consequently, the fluid-medium interface 510 is maintained in one location, preferably at or near the tops 520 of the fluid-support-structures 115.

Figure 7:
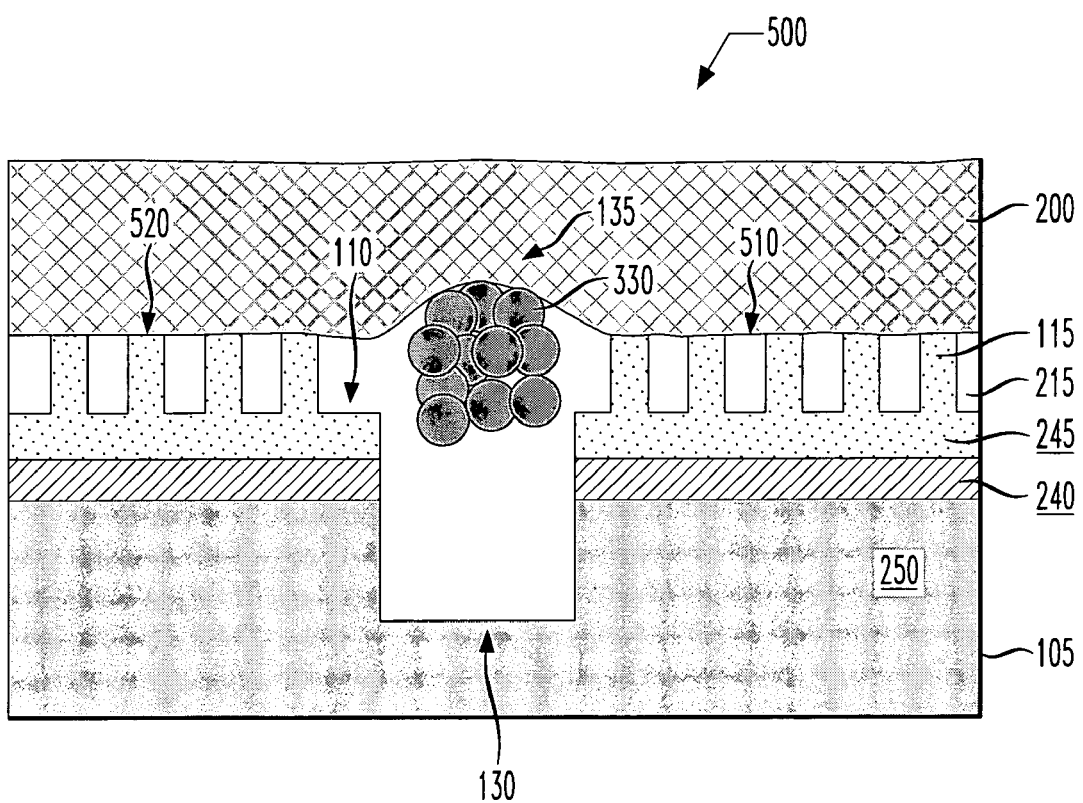

FIG. 7 also illustrates communicating the medium 215 by diffusing gas 330 between the fluid 200 and the well 130. In some cases, the gas 330 can diffuse out of the fluid 200 and into the well 130 because of a change in the temperature or pressure of the fluid 200. In other cases, the apparatus 500 can move between fluids 200 that have different amounts of gas 330 dissolved therein, thereby causing gas to diffuse out of the fluid 200. As illustrated in FIG. 7, gas 330 diffusing out of the fluid 200 prefers entering the well 130 to entering the fluid-support-structures 115. Consequently, the location of the fluid-medium interface 510 is less disturbed as compared to a well-free apparatus where the gas can enter into or forms on the tops of fluid-support-structures.

Figure 8:
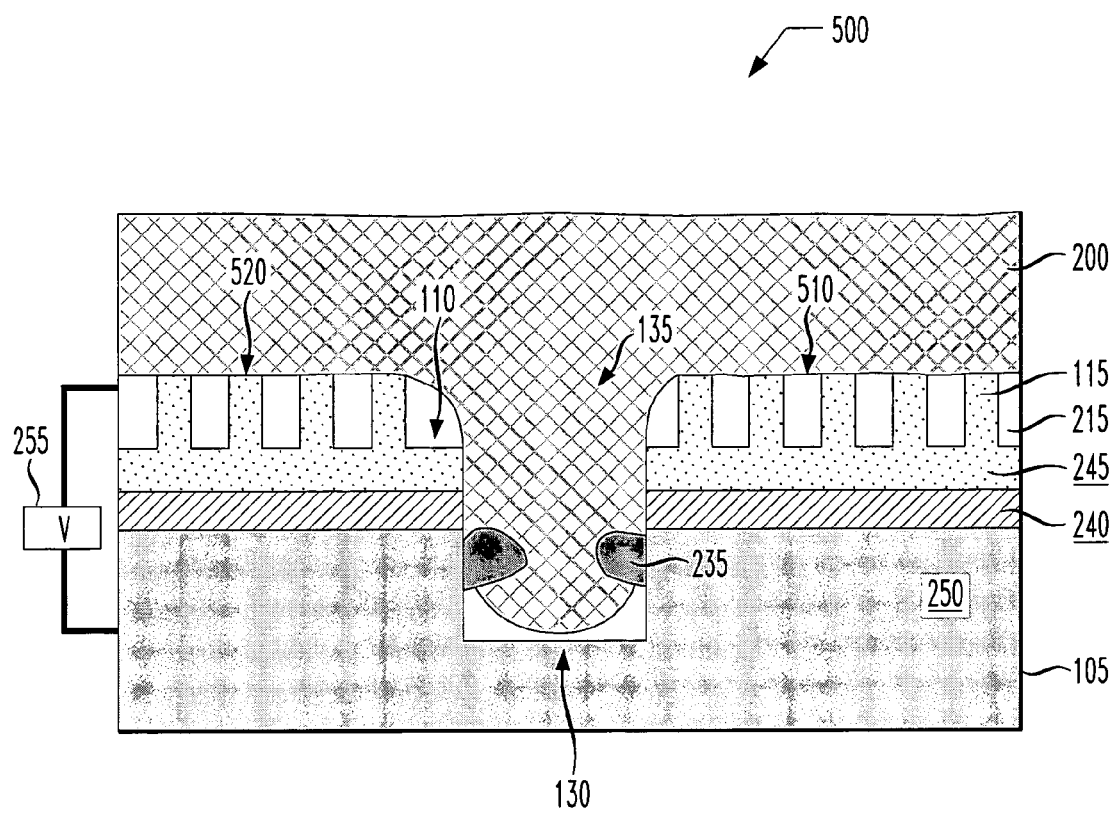

Illustrated in FIG. 8, while maintaining reference to FIG. 1-7, is communicating by electrolytically generating additional medium 235 in the well 130. As discussed above, in the context of FIG. 2, the apparatus 500 can comprise an electrical source 255 configured to apply a voltage between upper and lower conductive layers 245, 250 that are separated by an insulating layer 240. For instance, when the fluid 200 penetrates into the well 130 and below the insulating layer 240, the fluid 200 can complete an electrical connection between the upper and lower conductive layers 245, 250. Consequently, portions of the fluid 200 can undergo electrolysis and be converted into the additional medium 235. The additional medium 235, in turn, can be expelled into the fluid-support-structures 115, thereby maintaining the location of the fluid-medium interface 510. In some cases electrolysis is continued for a sufficient period that the additional medium 235 produced pushes the fluid 200 out of the well 130. Consequently, the electrical connection is broken and electrolysis stops.

It would be readily apparent to one of ordinary skill in the art that the above-described methods to control the flow resistance of the fluid 200 on the substrate surface 110 could be used alone or in combination with each other in a variety of different applications. In some cases, such as discussed in the context of FIG. 3, the method is used to control flow resistance in a microfluidic device. That is, the control of flow resistance is carried out while transporting a fluid through a channel having an interior surface having the fluid-support-structures and well. In other cases, such as illustrated in FIG. 4, the method is used to control flow resistance in an apparatus, such as a vehicle, moving through a fluid. That is, controlling flow resistance is done while moving a body through the fluid, the body having an exterior surface with the fluid-support-structures and wells.

Yet another embodiment of the present invention is a method of manufacture. FIGS. 9-14 illustrate plan and cross-sectional views of selected stages in an exemplary method of manufacturing an apparatus 900 according to the principles of the present invention. Any of the above-discussed embodiments of the apparatuses shown in FIG. 1-8 can be made by the method. The same reference numbers are used to depict analogous structures introduced in FIGS. 1-8.

Figure 9:
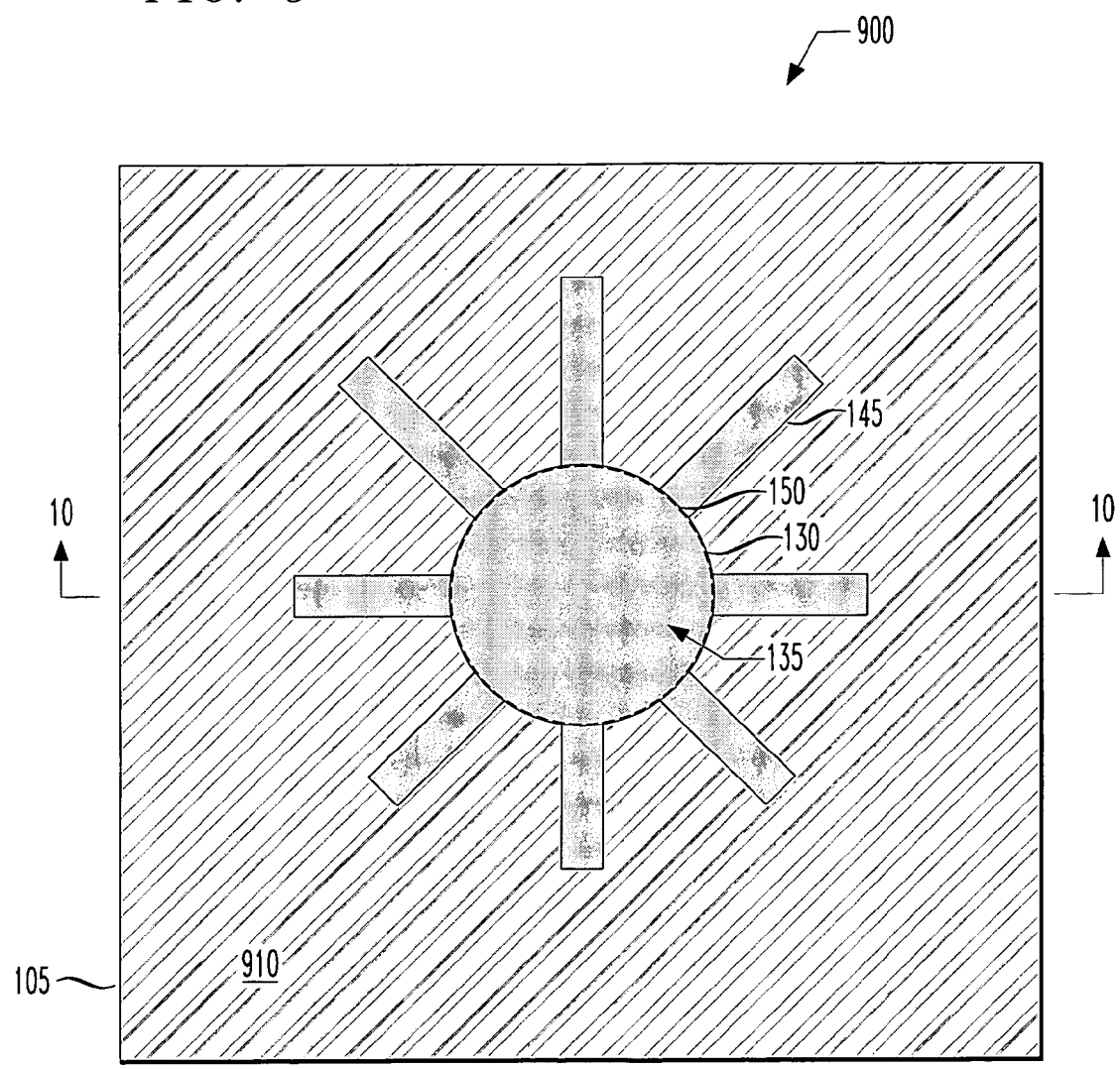
FIGS. 9-12 illustrate plan and cross-sectional views of selected stages in an exemplary method of manufacture according to the present invention.
Figure 10:
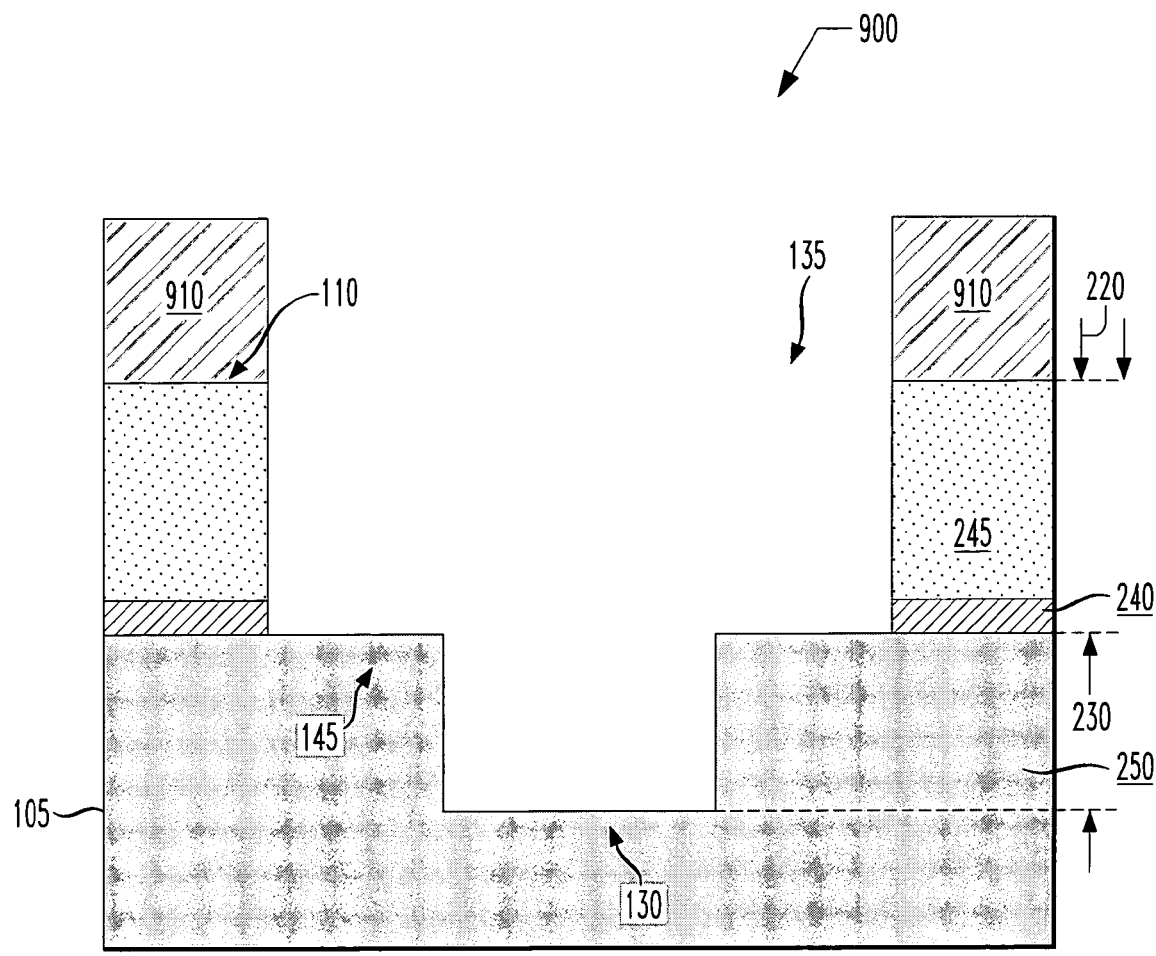

FIG. 9 presents a plan view of the partially-constructed apparatus 900, and FIG. 10 presents a cross-sectional view through view line 10-10. FIGS. 9 and 10 depict the apparatus 900 after forming a well 130 in a substrate 105. The well 130 has an opening 135 on a surface 110 of the substrate 105. Of course a plurality of wells can be formed in the substrate, if desired. In some cases, the well 130 is formed by drilling the substrate 105. In other cases, the well 130 is formed by using conventional photolithographic and wet or dry etching procedures, for example deep reactive ion etching, to remove portions of the substrate 105. As illustrated in FIGS. 9-10, in the latter case, a conventional photoresist 910 on the surface 110 can be used to advantageously cover those portions of the substrate 105 that are not etched when the well 130 is formed. In some preferred embodiments, the method includes forming arms 145 as part of the same etch process as used to form the wells 130. In other instances, if desired, the arms 145 can be formed separate from the steps to form the well 130. For example, in some cases, the well 130 is formed by drilling and the arms 145 are formed by dry etching.

As further illustrated in FIG. 10, in some preferred embodiments, the substrate 105 comprises a planar substrate, and more preferably, a stack of planar substrates, such as provided in a silicon-on-insulator (SOI) substrate. In some cases, such as illustrated in FIG. 10, the well 130 is formed to a depth 220 that penetrates an upper conductive layer 245, insulating layer 240 and lower conductive layer 250 of the substrate 105. In some cases, where the depth 220 of the well 130 is greater than 50 microns, it is preferable to form the well by drilling. In other cases, where the depth 220 of the well 130 is 50 microns or less, it can be advantageous to form the well 130 by etching. In some instances, such as when the well 130 is formed by drilling and the arms 145 are formed by dry etching, the depth 220 of the well 130 is greater than a depth 230 of the arms 145.

Figure 11:
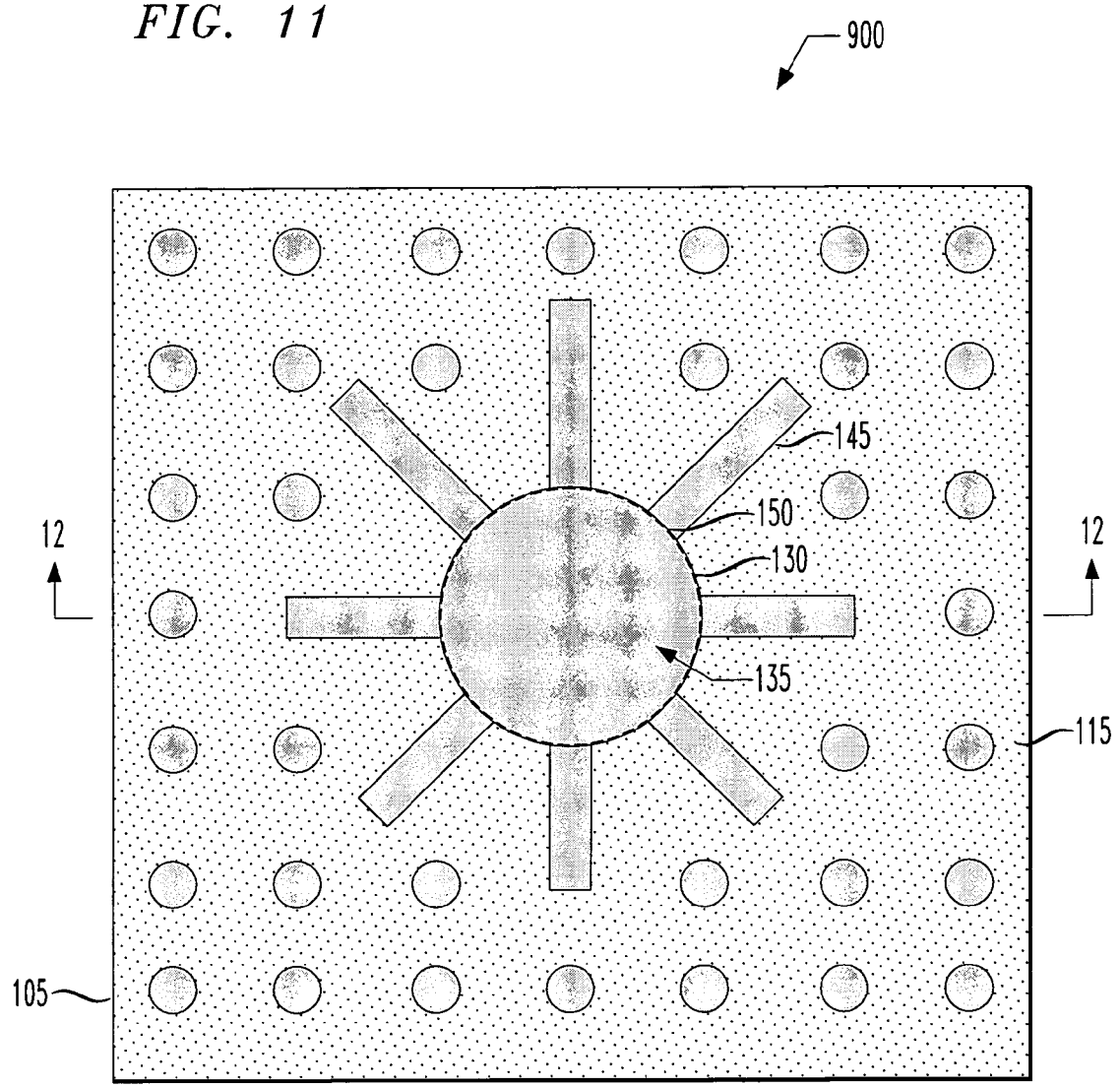

Turning now to FIG. 11, illustrated is a plan view of the apparatus 900 after forming a plurality of fluid-support-structures 115 on the surface 110. As discussed above, each of the fluid-support-structures 115 has at least one dimension of less than one millimeter. That is, the fluid-support-structures 115 are at least microstructures, and in some cases, are nanostructures. As illustrated, the fluid-support-structures 115 can be formed into posts. The fluid-support-structures 115 can be formed using conventional photolithographic and etching procedures, to remove portions of the substrate 105. Alternatively, the fluid-support-structures 115 can be formed by patterning the surface 110 with a photoresist, electroplating a metal such as nickel over the pattern, and removing the photoresist. Other conventional methods of forming the fluid-support-structures 115 would be readily apparent to one of ordinary skill in the art.

Figure 12:
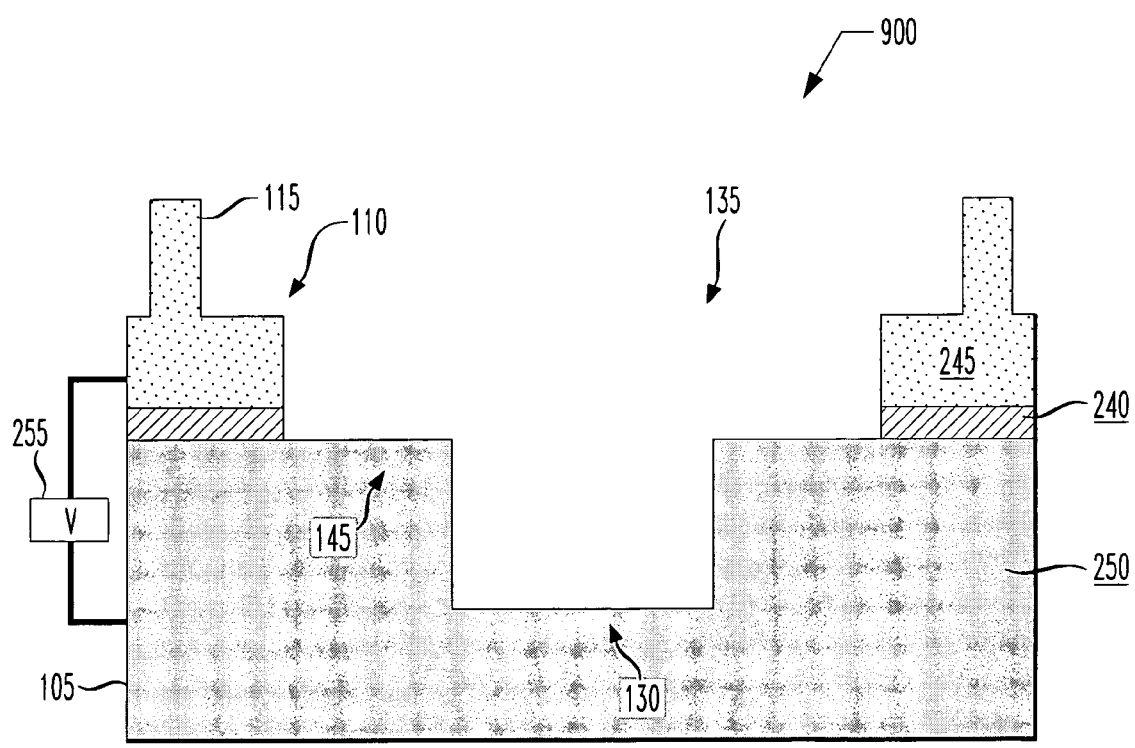

Turning now to FIG. 12, shown is a cross-sectional view of the apparatus 110 at the same stage of manufacture as depicted in FIG. 11, through view line 12-12 in FIG. 11. As illustrated, the fluid-support-structures 115 and the well 130 are configured to allow a medium 215 to communicate between the fluid-support-structures 115 and the well 130. Communication can be facilitated as shown in FIG. 12 by forming the well 130 so that it is below the substrate surface 110 after removing portions of the substrate 105 to form the fluid-support-structures 115. As further illustrated in FIG. 12, embodiments the method can further comprise coupling an electrical source 255 to the upper conductive layer 245 and to a lower conductive layer 250 of the substrate 105, with insulating layer 240 located there-between.

Although the present invention has been described in detail, those of ordinary skill in the art should understand that they could make various changes, substitutions and alterations herein without departing from the scope of the invention.

What is claimed is:

1. An apparatus comprising:
a substrate having a surface configured to accommodate a fluid thereover, wherein said surface comprises:
a plurality of fluid-support-structures on said surface, each of said fluid-support-structures having at least one dimension of less than one millimeter; and
a well in said substrate, wherein said well has an opening on said surface;
wherein said fluid-support-structures and said well are configured to allow a medium to communicate between said fluid-support-structures and said well, when said fluid contacts said fluid-support-structures, and
wherein said surface is an interior surface of a channel configured to transport said fluid.

2. An apparatus comprising:
a substrate having a surface configured to accommodate a fluid thereover, wherein said surface comprises:
a plurality of fluid-support-structures on said surface, each of said fluid-support-structures having at least one dimension of less than one millimeter; and
a well in said substrate, wherein said well has an opening on said surface;
wherein said fluid-support-structures and said well are configured to allow a medium to communicate between said fluid-support-structures and said well, when said fluid contacts said fluid-support-structures, and
wherein said surface is located on an exterior surface of a body configured to move through said fluid.

3. The apparatus of claim 2, wherein at least one lateral dimension of said well is less than a capillary length of said fluid.

4. The apparatus of claim 2, wherein at least one lateral dimension of said well is from about 10 to about 100 times greater than a separation between adjacent ones of said fluid-support-structures.

5. The apparatus of claim 2, wherein said substrate comprises an insulating layer located between an upper conductive layer and a lower conductive layer, and an electrical source configured to apply a voltage between said upper and lower conductive layer.

6. A method, comprising:
controlling a flow resistance of a fluid disposed on a surface of a substrate, comprising:
contacting said fluid with a plurality of fluid-support-structures on said surface, each of said fluid-support-structures having at least one dimension of less than one millimeter and a medium located there-between, thereby forming a medium-fluid interface; and
communicating said medium between said fluid-support-structures and a well in said substrate, thereby stabilizing a location of said medium-fluid interface over said surface, wherein said communicating includes diffusing gas from between said fluid and said well.

7. A method, comprising:
controlling a flow resistance of a fluid disposed on a surface of a substrate, comprising:
contacting said fluid with a plurality of fluid-support-structures on said surface, each of said fluid-support-structures having at least one dimension of less than one millimeter and a medium located there-between, thereby forming a medium-fluid interface; and
communicating said medium between said fluid-support-structures and a well in said substrate, thereby stabilizing a location of said medium-fluid interface over said surface, wherein said communicating includes electrolytically generating additional medium in said well.

8. A method, comprising:
controlling a flow resistance of a fluid disposed on a surface of a substrate, comprising:
contacting said fluid with a plurality of fluid-support-structures on said surface, each of said fluid-support-structures having at least one dimension of less than one millimeter and a medium located there-between, thereby forming a medium-fluid interface; and
communicating said medium between said fluid-support-structures and a well in said substrate, thereby stabilizing a location of said medium-fluid interface over said surface, wherein said controlling is done while transporting said fluid through a channel having an interior surface having said fluid-support-structures and said well.

9. A method, comprising:
controlling a flow resistance of a fluid disposed on a surface of a substrate, comprising:
contacting said fluid with a plurality of fluid-support-structures on said surface, each of said fluid-support-structures having at least one dimension of less than one millimeter and a medium located there-between, thereby forming a medium-fluid interface; and communicating said medium between said fluid-support-structures and a well in said substrate, thereby stabilizing a location of said medium-fluid interface over said surface, wherein said controlling is done while moving a body through said fluid, said body having an exterior surface having said fluid-support-structures and said well.

* * * * *